US009783456B1

(12) United States Patent
Zhou

(10) Patent No.: US 9,783,456 B1
(45) Date of Patent: Oct. 10, 2017

(54) METHOD FOR INHIBITING CELL GROWTH USING ANTI-ERBB-3 AND ANTI-ERBB-2 ANTIBODIES

(75) Inventor: Mingdong Zhou, La Jolla, CA (US)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 46 days.

(21) Appl. No.: 09/979,809

(22) PCT Filed: Jun. 16, 2000

(86) PCT No.: PCT/AU00/00671

§ 371 (c)(1),
(2), (4) Date: Mar. 5, 2002

(87) PCT Pub. No.: WO00/78347

PCT Pub. Date: Dec. 28, 2000

(30) Foreign Application Priority Data

Jun. 18, 1999 (AU) .......................................... 1057

(51) Int. Cl.
A61K 39/395 (2006.01)
C03C 17/34 (2006.01)

(52) U.S. Cl.
CPC ................ C03C 17/3411 (2013.01)

(58) Field of Classification Search
USPC ............................................. 530/350; 514/2
See application file for complete search history.

(56) References Cited

U.S. PATENT DOCUMENTS

| | | | |
|---|---|---|---|
| 5,183,884 A | 2/1993 | Kraus et al. | |
| 5,480,968 A | 1/1996 | Kraus et al. | |
| 5,578,482 A | 11/1996 | Lippman et al. | ......... 435/240.1 |
| 5,686,102 A | 11/1997 | Gross et al. | |
| 5,736,154 A | 4/1998 | Fuisz | |
| 5,741,511 A | 4/1998 | Lee et al. | |
| 5,820,859 A | 10/1998 | Kraus et al. | ............... 424/143.1 |
| 5,886,039 A | 3/1999 | Kock et al. | |
| 5,941,868 A | 8/1999 | Kaplan et al. | |
| 5,968,511 A * | 10/1999 | Akita et al. | ............... 424/141.1 |
| 6,197,801 B1 | 3/2001 | Lin | |
| 6,258,374 B1 | 7/2001 | Friess et al. | |
| 7,285,649 B2 | 10/2007 | Akita et al. | |
| 7,919,098 B2 | 4/2011 | Zhou | |
| 2004/0197332 A1 | 10/2004 | Ullrich et al. | |
| 2005/0136494 A1 | 6/2005 | Akita et al. | |
| 2011/0229478 A1 | 9/2011 | Zhou | |

FOREIGN PATENT DOCUMENTS

| | | |
|---|---|---|
| EP | 0 896 586 | 6/1991 |
| EP | 0 502 927 | 10/1997 |
| WO | WO A 9102062 | 2/1991 |
| WO | WO A 9108214 | 6/1991 |
| WO | WO-97/35885 | 10/1997 |
| WO | WO 97/35885 | 10/1997 |
| WO | WO 98/02540 | 1/1998 |
| WO | WO 98/17797 | 4/1998 |
| WO | WO A 9830704 | 7/1998 |
| WO | WO A 9835036 | 8/1998 |
| WO | WO 01/87334 | 11/2001 |
| WO | WO 03/013602 | 2/2003 |
| WO | 03/080835 A1 | 10/2003 |
| WO | WO 2006/091209 | 8/2006 |
| WO | WO 2008/100624 | 8/2008 |

OTHER PUBLICATIONS

Cooper (The Cell: A Molecular Approach, 2nd Ed, 2000, ASM Press, Washington, DC, section 13: Cell Signaling; Receptor Protein-Tyrosine Kinases, 7 pages).*
Holbro et al (PNAS, 2003, 100:8933-8938).*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Curti (Crit. Rev. in Oncology/Hematology, 1993, 14:29-39).*
Lab Vision NeoMarkers data sheet (Ab105).*
Lab Vision NeoMarkers Data Sheet.*
Faress et al (J Appl Physiol, 2007, 103:2077-2083).*
Chan et al (J of Biol Chem, 1995, 270:22608-22613).*
Lab Vision NeoMarkers Data Sheet (Ab105/ H3.105.5 ) (one page, No Date).*
Chen et al, 1996, J Biol Chem, 271:7620-7629.*
Lewis et al I (Cancer immunology Immunotherapy, 1993, 37:255-263).*
Lewis et al II (Cancer Research, 1996, 56:1457-1465).*
Stancovski et al (PNAS, 1991, 88:8691-8695).*
Pinkas-Kramarski et al (Oncogene, 1998, 16:1249-1258).*
Drebin et al (Oncogene, 1988, 2:273-277, in the IDS).*
Wilken et al, Journal of Ovarian Research, 2010, 3:7-9.*
Pattarozzi et al, Molecular Pharmacology, 2007, 73:191-202.*
Emde et al, Translational Oncology, 2011, 4:293-300.*
Cohen et al (J Biological Chemistry, 1996, 271:30897-30903).*
Klapper et al. "A Subclass of Tumor-Inhibitory Monoclonal Antibodies to ErbB-2/HER2 Blocks Crosstalk with Growth Factor Receptors" Oncogene 14:2099-2109 (1997).
Klapper et al. "The ErbB-2/HER2 Oncoprotein of Human Carcinomas May Function Solely As a Shared Coreceptor for Multiple Stroma-Derived Growth Factors" Proc. Natl. Acad. Sci. USA 96:4995-5000 (1999).
Park et al. "Induction of the Tat-Binding Protein 1 Gene Accompanies the Disabling of Oncogenic ErbB Receptor Tyrosine Kinases" Proc. Natl. Acad. Sci. USA 96:6434-6438 (1999).
Pinkas-Kramarski et al. "The Oncogenic ErbB-2/ErbB-3 Heterodimer Is a Surrogate Receptor of the Epidermal Growth Factor and Betacellulin" Oncogene 16:1249-1258 (1998).
Ram et al. "Mitogenic Activity of Neu Differentiation Factor/Heregulin Mimics that of Epidermal Growth Factor and Insulin-Like Growth Factor-I in Human Mammary Epithelial Cells" J. Cell Physiol. 169:589-596 (1996).

(Continued)

Primary Examiner — Laura B Goddard
(74) Attorney, Agent, or Firm — Jones Day

(57) ABSTRACT

Methods for arresting or inhibiting cell growth, particularly cancer cell growth, comprising preventing or reducing ErbB-2/ErbB-3 heterodimer formation, or interfering with ErbB-2/ErbB-3 heterodimer conformation in a cell and agents which prevent or reduce ErbB-2/ErbB-3 heterodimer formation or interface with ErbB-2/ErbB-3 heterodimer conformation in a cell thereby arresting or inhibiting the growth of the cell.

20 Claims, 6 Drawing Sheets

(56) References Cited

OTHER PUBLICATIONS

Sliwkowski et al. "Co-Expression of erbB2 and erbB3 Proteins Reconstitutes a High Affinity Receptor for Heregulin" J. Biolog. Chem. 269(20):14661-14665 (1994).
Vijapurkar et al. "Mutation of a Shc Binding Site Tyrosine Residue in ErbB3/HER3 Blocks Heregulin Dependent Activation of Mitogen-Activated Protein Kinase" J. Biol. Chem. 273(33):20996-21002 (1998).
Supplementary European Search Report for application No. 00 93 6539, mailed on Apr. 29, 2005, 4 pages.
Alimandi et al., 1995, "Cooperative signaling of ErbB3 and ErbB2 in neoplastic transformation and human mammary carcinomas." Oncogene 10:1813-1821.
Auerbach & Auerbach, 1994, "Angiogenesis inhibition: A review." Pharmacol. Ther. 63(3):265-311.
Bei et al 1999, "Immune Responses to all ErbB family receptors detectable in serum of cancer patients." Oncogene 18(6):1267-1275.
Drebin et al., 1988, "Monoclonal antibodies reactive with distinct domains of the neu oncogene-encoded p185 molecule exert synergistic anti-tumor effects in vivo." Oncogene 2:273-277.
Fendly et al., 1990, "Characterization of Murine Monoclonal Antibodies Reactive to Either the Human Epidermal Growth Factor Receptor or HER2/neu Gene Product." Cancer Res. 50:1550-1558.
Gellner & Brenner, 1999, "Analysis of 148 kb of genomic DNA around the wnt1 locus of Fugu rubripes." Genome Res 9(3):251-258.
Genbank Accesion No: AF056116, "Fugu rubripcs serine/threonine kinase receptor type1, All-1 related protein (ALR), fugu hedgehog (fhh), Ikaros-like, wnt1, wnt10b, ARF3, erbB3, PAS1, and L41 ribosomal protein genes, complete cds; LRP1 gene, partial cds; and unknown genes," dated Apr. 15, 1999.
Genbank Accesion No: M29366, "Human epidermal growth factor receptor (ERBB3) mRNA, complete cds," dated Apr. 23, 1993.
Genbank Accession No: U29339, "Rattus norvegicus ErbB3/Her3 precursor mRNA, complete cds," dated Dec. 5, 2001.
Hamid, 2004, "Emerging Treatments in Oncology: Focus on Tyrosine Kinase (erbB) Receptor Inhibitors." J Am. Pharm Assoc. 44:52-58.
Hellyer et al., 1995, "Cloning of the rat ErbB3 cDNA and characterization of the recombinant protein." Gene 165(2):279-284.
Hudson & Souriau, 2003, "Engineered antibodies." Nat. Med. 9:129-134.
International Preliminary Examination Report of PCT/AU00/00671, dated Oct. 9, 2001, Published as WO 00/078347.
International Search Report of Application No. PCT/AU00/00671, dated Aug. 30, 2000.
International Search Report of Application No. PCT/CN03/00217, dated Jun. 5, 2003.
Kasprzyk et al., 1992, "Therapy of an Animal Model of Human Gastric Cancer Using a Combination of Anti-erbB-2 Monoclonal Antibodies." Cancer Res. 52:2771-2776.
Kraus et al., 1989, "Isolation and characterization of ERBB3, a third member of the ERBB/epidermal growth factor receptor family: evidence for overexpression in a subset of human mammary tumors." Proc. Natl. Acad. Sci. 86:9193-9197.
Lee et al., 2001, "A naturally occurring secreted human ErbB3 receptor isoform inhibits heregulin-stimulated activation of ErbB2, ErbB3, and ErbB4." Cancer Res 61:4467-4473.
Lilleiioj et al., 1993, "Adjuvanticity of dimethyl dioctadecyl ammonium bromide, complete Freund's adjuvant and Corynebacterium parvum with respect to host immune response to coccidial antigens." Avian Dis 37(3):731-740.
Mendrola et al., 2002, "The Single Transmembrane Domains of ErbB Receptors Self-associate in Cell Membranes." J. Biol. Chem. 27:4704-4712.
Plowman et al., 1990, "Molecular cloning and expression of an additional epidermal growth factor receptor-related gene." Proc. Natl. Acad. Sci 87:4905-4909.
Ratiff et al, 1992, "Role of the immune response in BCG for bladder cancer." Eur. Urol. 2 (Suppl):17-21.
Schaefer et al., 2006, "Potential use of humanized antibodies in the treatment of breast cancer." Expert Rev. Anticancer. Ther. 6:1065-1074.
Stern & Herrman, 2005, "Overview of monoclonal antibodies in cancer therapy: present and promise." Crit. Rev in Oncology/Hematology 54:11-29.
Supplementary European Search Report for European Application No: EP 00 93 6539, mailed on Apr. 29, 2005.
Ye et al., 1999, "Augmentation of a humanized anti-HER2 mAb 4D5 induced growth inhibition by a human-mouse chimeric anti-EGF receptor mAb C225." Oncogene 18:731-738.
Yeon & Pegram, 2005, "Anti-crbB-2 antibody trastuzumab in the treatment of HER2-amplified breast cancer." Invest. New Drugs 23:391-409.
Chen et al., 1996, "An Immunological Approach Reveals Biological Differences between the Two NDF/Heregulin Receptors, ErhB-3 and ErhB-4." J. Biol. Chem. 271(13):7620-7629.
Lab Vision Neomarkers Data Sheet (Ab105) "c-erbB-3/Her-3 Ab-5 (Clone H3.105.5; same as Ab105)" Accessed Mar. 26, 2009 from http://www.labvision.com.
Pinkas-Kramarski et al., 1998, "The oncogenic ErbB-2/ErbB-3 heterodimer is a surrogate receptor of the epidermal growth factor and betacellulin." Oncogene 16:1249-1258.
Vadlamudi et al., 1999, "Regulation of Cyclooxygenase-2 pathway by HER2 receptor." Oncogene 18:305-314.
Stoica et al. 2003, "Effect of estradiol on estrogen receptor-alpha gene expression and activity can be modulated by the ErbB2/PI 3-K/Akt pathway" Oncogene 22, pp. 7998-8011.
Bandyopadhyay et al., 1998, "Physical interaction between epidermal growth factor receptor and DNA-dependent protein kinase in mammalian cells" J. Biol. Chem. 273, pp. 1568-1573.
Hudziak et al., 1989, Molecular and Cellular Biology 9, pp. 1165-1172.
Xu et al., 1993, "Antibody-induced growth inhibition is mediated through immunochemically and functionally distinct epitopes on the extracellular domain of the c-erbB-2 (HER-2/neu) gene product p185" Int. J. Cancer 53, pp. 401-408.
Levy and Miller, 1983, "Biological and clinical implications of lymphocyte hybridomas: tumor therapy with monoclonal antibodies" Ann. Rev. Med. 34, pp. 107-116.
Schroff et al., 1984, "T65 antigen modulation in a phase 1 monoclonal antibody trial with chronic lymphocytic leukemia patients" The Journal of Immunology 133, pp. 1641-1648.
Burgess et al., 2003, "An Open-and-Shut Case? Recent Insights into the Activation of EGF/ErbB Receptors" Molecular Cell 12, pp. 541-552.
Wang et al., 1998, "Reciprocal interactions between β1-integrin and epidermal growth factor receptor in three-dimensional basement membrane breast cultures: A different perspective in epithelial biology" PNAS 95, 14821-14826.
Relevant Documents in European Opposition Proceeding in connection with European Patent Application No. EP1187634. No date.
Pegram et al. 1999, "Inhibitory e ects of combinations of HER-2/neu antibody and chemotherapeutic agents used for treatment of human breast cancers" Oncogene 18, pp2241-2251.
Koseielny et at. 1998, "Prognostic Importance of Low c-erbB2 Expression in Breast Tumors" J. of the National Cancer Institute, vol. 90. No. 9, p712.
Barron et al. 2009. "HER2 Testing and Subsequent Trastuzumab Treatment for Breast Cancer in a Managed Care Environment" The Oncologist, 14:760-768.
Lemoine et al., 1992, "Expression of the ERBB3 gene product in breast cancer" Br. J. Cancer, 66:1116-1121.
Berchuck et al., 1990, "Overexpression of HER-2/neu is Associated with Poor Survival in Advanced Epithelial Ovarian Cancer" Cancer Research, 50:4087-4091.
Knowlden et al., 1998. "c-erbB3 and c-erbB4 expression is a feature of the endocrine responsive phenotype in clinical breast cancer" Oncogene, 17:1949-1957.

(56) References Cited

OTHER PUBLICATIONS

Thermo Scientific Product Data Sheet, "HER-2/ErbB Antibody (N12)," Retrieved from the Internet: URL:http://www.pierce-antibodies.com/products/printProductDetail/printProductDetails.cfm?js=1&format=extended&catnbr=MA5-12998 [retrieved on Apr. 7, 2015].

ATCC Information on Caov-3, [retrieved on May 18, 2015], retrieved from the internet: <http://www.lgcstandards-atcc.org/products/all/HTB-75.aspx?geo_country=de>.

Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol., 17(9):2639-2648 (1999).

European Patent Office, Notice of Opposition, issued in Application No. 07119791.7, dated Jun. 1, 2015.

Karlan et al., "Glucocorticoids stabilize HER-2/neu messenger RNA in human epithelial ovarian carcinoma cells," Gynecol. Oncol., 53(1):70-77 (1994).

Lewis et al., "Growth regulation of human breast and ovarian tumor cells by heregulin: Evidence for the requirement of ErbB2 as a critical component in mediating heregulin responsiveness," Cancer Res., 56(6):1457-1465 (1996).

\* cited by examiner a b a b

METHOD FOR INHIBITING CELL GROWTH USING ANTI-ERBB-3 AND ANTI-ERBB-2 ANTIBODIES

RELATED APPLICATIONS

This application is a 371 national stage application of international application Serial No. PCT/AU00/00671 filed Jun. 16, 2000, which claims the benefit of priority to AUSTRALIA PQ 1057 filed Jun. 18, 1999.

TECHNICAL FIELD

The present invention relates to methods for arresting cell growth applicable to cancer treatment and therapy.

BACKGROUND ART

Cancer is a major lethal disease for humans and is caused by physiologically-uncontrolled cell proliferation which affects normal physiological conditions of human body resulting in serious pathological reactions often leading to death. Although tremendous efforts on cancer studies and treatments have been made, presently, cancer is still the major cause of death to humans. There are multiple approaches to treat cancer patients including surgery, radiation therapy, and chemotherapy. As the first two methods are not able to completely eliminate cancer cells in patients, the latter approach is commonly used to control cancer cell growth with or without other treatments. Anti-cancer compounds used in patients are often targeting prevention of cancer cell proliferation or killing dividing cells. When the compounds are toxic to cancer cells, they may also severely affect normal dividing cells which are necessary for human life. Therefore, one of main directions in cancer studies is to find methods to specifically block or kill cancer cells without affecting normal cell proliferation. There is a demand, now, for such treatment on cancer patients.

ErbBs are class one receptor protein tyrosine kinases. ErbB-mediated cell signalling plays a critical role in embryo development and adult organ function. On a cellular level, ErbB receptors have been shown to mediate signals for cell proliferation, differentiation, migration, and cell structure reorganisation. There are four structurally similar ErbB members, ErbB-1, ErbB-2. ErbB-3 and ErbB-4. The epidermal growth factor (EGF) is one of several ligands that bind ErbB-1. ErbB-3 or ErbB-4 also bind several ligands, including neuregulin-1 (NRG-1). To date, no ligand for ErbB-2 has been identified. However. ErbB-2 serves as an heterodimer partner for ErbB-3, ErbB-4 or ErbB-1, and is critically involved in NRG-1-activated cell signalling.

In vivo studies using gene targeting experiments indicate that developmental defects resulting from inactivation of ErbB-2 are similar to those observed in NRG-1-inactivated animals. Both animals show defects in the neural crania ganglia and heart trabeculae development. Furthermore, ErbB-3 or ErbB-4 gene-inactivated mice have similar or overlapping phenotypes to NRG-1 or ErbB-2 knockout mice.

In addition to its role in development, the human ErbB-2 gene is frequently amplified and its encoded protein is over-expressed in a variety of human carcinomas. Early research on ErbB-2 discovered that an oncogenic point mutation resulted in the formation of ErbB-2 homodimers that in turn caused significant phosphorylation of the tyrosine residues on the intracellular domain. While no corresponding point mutation has been found in ErbB-2 over expressing human carcinomas, the upregulation of ErbB-2 results in the formation of homodimers that in turn increases the tyrosine phosphorylation of its intracellular domain. This process is hypothesised to be the start of a signal cascade that triggers cell transformation and/or growth, and thus initiate tumourigenesis. There is evidence, however, to contradict the hypothesis that ErbB-2 homodimers are responsible for the initiation of tumourigenesis: i) some ErbB-2 mutants that are engineered to enhanced dimerisation and self-phosphorylation have no effect on cell transformation; ii) antibodies that bind to the extracellular domain of ErbB-2 and presumably promote homodimerisation result in ErbB-2-expressing cancer cell growth promotion, whereas others inhibit cancer cell growth. These data indicate that homodimerisation of ErbB-2 is insufficient for cell growth promotion or cell transformation, and other conditions, possibly involving specific dimer orientation or conformation, are required.

ErbB-2 acts as a heterodimer partner for the ligand-binding ErbB-3 or ErbB-4 receptors. The ligand. NRG-1, has been identified to have two independent receptor binding sites: one that has a high affinity for ErbB-3 or ErbB-4, and the other that has a low but non-specific affinity for all ErbB members. Thus, the exposure of NRG-1 to cells expressing ErbB-3/4 and ErbB-2 would result in heterodimers of ErbB-2 and ErbB-3/4. In the absence of the ligand, however, it is unclear whether ErbB-2 has an affinity with other ErbB receptors, and it is possible that such an interaction could be involved in the initiation of cancer. Amongst all the ErbB receptors, ErbB-3 is unique because: i) ErbB-2 preferentially forms heterodimers with ErbB-3; ii) co-transfection of NIH3T3 cells with ErbB-2 and ErbB-3 results in much higher levels of cell transformation than that of transfection with ErbB-2 alone; iii) in ErbB-2 over-expression-associated breast cancer cells. ErbB-3 is also highly expressed: iv) ErbB-3 is also over expressed in ErbB-2-over expressing tumour cells from ErbB-2 transgenic mice.

The present inventors studied the role of ErbBs and their interaction in cell growth and inhibition. Importantly, it was found that homo- and heterodimer formation of ErbBs can play a role in cell proliferation, particularly in cancer cells.

DISCLOSURE OF INVENTION

The present inventors have surprisingly found that ErbB-2 expression leads to inhibition of oncogenic Ras-mediated cell transformation. Furthermore, the present inventors have found that ErbB-2/ErbB-3 heterodimer formation leads to cell growth stimulation, particularly in cancer cells.

In a first aspect, the present invention provides a method of arresting or inhibiting cell growth, the method comprising preventing or reducing ErbB-2/ErbB-3 heterodimer formation in a cell thereby arresting or inhibiting growth of the cell.

Preferably, the cell is a cancer cell, more preferably a human breast cancer cell.

One way to carry out the method according to the present invention is to treat the cell with a suitable agent. Preferably, the agent is selected from molecules which bind to ErbB-2 or ErbB-3 and block, interrupt or interfere with ErbB-2/ErbB-3 heterodimer formation or conformations resulting in cell growth inhibition.

In one preferred form, the agent is a combination of an anti-ErbB-2 extracellular domain antibody and an anti-ErbB-3 antibody. Such a combination has been found to produce an additive or synergistic effect in of arresting, inhibiting or suppressing cell growth.

A combination of the anti-ErbB-2 antibody N12 and the anti-ErbB-3 antibody H3.105.5 have been found to be particularly suitable for the present invention.

The ErbB-2 dimerisation can be caused by multiple mediators, for example, a high level of ErbB-2 expression, antibodies binding with the ErbB-2 extracellular domain. ErbB-2-activated cell growth arrest can overcome the oncogenic Ras-activated cell transformation, suggesting a therapeutic usage of the ErbB-2 dimerisation. The present inventors have found that ErbB-2 actually interacts with other ErbB members, such as ErbB-3. Furthermore, ErbB-2/ErbB-3 complex formation was found to be independent of ligand (neuregulin 1) stimulation. The presence of ErbB-3 in ErbB-2-expressing cells was able to sufficiently block ErbB-2 homodimer-activated cell growth arrest. In fact, ErbB-3 is usually expressed in ErbB-2-expressing cancer cells which allows cancer cell growth. This discovery indicates that molecules which are able to block the interaction between ErbB-2 and other membrane proteins will assist or enhance ErbB-2 homodimerisation. As native ErbB-2 is the major form over-expressed in cancer cells, this discovery allows new methods to treat cancer patients carrying ErbB-2-expressing cancer cells to be developed.

In a second aspect, the present invention provides a method of cancer therapy, the method comprising preventing or reducing ErbB-2/ErbB-3 heterodimer formation in a cancer cell of a patient thereby arresting or inhibiting the growth of the cancer cell.

Preferably, the cell is a cancer cell, more preferably a human breast cancer cell.

Preferably the cancer therapy involves administering one or more agents capable of preventing or reducing ErbB-2/ErbB-3 heterodimer formation in the cancer cell without substantially adversely effecting normal cells in the patient. The one or more agents may act by preventing or reducing the interaction of ErbB-2 with ErbB-3 in the cancer cells.

Preferably, the agent is selected from molecules which bind to ErbB-2 or ErbB-3 and block, interrupt or interfere with ErbB-2/ErbB-3 heterodimer formation or conformations resulting in cell growth inhibition.

In one preferred form, the agent is a combination of an anti-ErbB-2 extracellular domain antibody and an anti-ErbB-3 antibody. Such a combination has been found to produce an additive or synergistic effect in of arresting, inhibiting or suppressing cell growth.

A combination of the anti-ErbB-2 antibody N12 and the anti-ErbB-3 antibody H3.105.5 have been found to be particularly suitable for the present invention.

It will be appreciated, however, that other antibodies which prevent or lower ErbB-2/ErbB-3 heterodimer formation in a cell would be suitable candidates for the present invention. For human clinical use, humanised antibodies would be more suitable so as to minimise complications from therapy. Techniques are well known for developing such antibodies and could be applied to develop suitable agents which block, interrupt or interfere with ErbB-2/ErbB-3 heterodimer formation or conformations in cells to arrest or inhibit cell growth.

Preferably the agent is one or more of compounds which cause a high level of ErbB-2 expression in a cancer cell, compounds which bind with the ErbB-2 extracellular domain such as antibodies and other ligands, and compounds which prevent or reduce ErbB-3 expression in a cell or which prevent the interaction of ErbB-3 with ErbB-2 in a cell. Other agents include DNA expression constructs containing cDNAs encoding proteins/peptides which can mediate or enhance the ErbB-2 homodimerisation or prevent or reduce the interaction between ErbB-2 and other ErbB members, such as ErbB-3. These compounds can be anti-ErbB-2 or anti-ErbB-3 antibodies. The DNA constructs can be delivered by gene therapy methods which include DNA transfection, infection with viruses carrying the cDNAs, or other DNA delivery methods or systems.

In a third aspect, the present invention consists in use of an agent which prevents or reduces ErbB-2/ErbB-3 heterodimer formation in a cell thereby arresting or inhibiting the growth of the cell in the manufacture of a medicament for cancer therapy.

In a fourth aspect, the present invention provides an anticancer agent comprising one or more compounds which prevent or reduce ErbB-2/ErbB-3 heterodimer formation in a cancer cell.

Preferably, the cell is a cancer cell, more preferably a human breast cancer cell.

Preferably, the agent comprises one or more compounds which bind to ErbB-2 or ErbB-3 and block, interrupt or interfere with ErbB-2/ErbB-3 heterodimer formation or conformations in a cell.

In one preferred form, the agent comprises a combination of an anti-ErbB-2 extracellular domain antibody and an anti-ErbB-3 antibody. More preferably, the antibody combination produces a synergistic effect in arresting or inhibiting cell growth.

A combination of the anti-ErbB-2 antibody N12 and the anti-ErbB-3 antibody H3.105.5 have been found to be suitable for the present invention.

It will be appreciated that other antibodies which prevent or lower ErbB-2/ErbB-3 heterodimer formation in a cell would be suitable candidates for the present invention. For human clinical use, humanised antibodies would be more suitable so as to minimise complications from therapy. Techniques are well known for developing such antibodies and could be applied to develop suitable agents which block, interrupt or interfere with ErbB-2/ErbB-3 heterodimer formation or conformations in cells to arrest or inhibit cell growth.

In a fifth aspect, the present invention consists in a method of testing or screening agents for suitability as anti-cancer agents, the method comprising exposing a cell expressing ErbB-2 and ErbB-3 to the agent and determining the extent of ErbB-2/ErbB-3 heterodimer in the cell, wherein, decreased ErbB-2/ErbB-3 heterodimer and/or cell transformation inhibition being indicative of anti-cancer potential of the agent.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood preferred forms will be described with reference to the accompanying drawings.

a) (top panel). Western blot analysis with anti-phosphotyrosine antibody. Note that ErbB-2 receptors were phosphorylated in ErbB-2 transfected cells, and NRG-1 enhanced the phosphorylation level of the receptors in ErbB-2/3 cotransfected cells.

a) (middle panel) Western blot analysis with anti-ErbB-2 antibody. ErbB-2 receptors were detected in ErbB-2 alone transfected and ErbB-2 with ErbB-3 cotransfected cells. NRG-1 also increased the interaction of ErbB-2 and ErbB-3.

a) (bottom panel) Western blot analysis with anti-ErbB-3 antibody. Except for ErbB-2 transfected cells, all other samples displayed a major ErbB-3 band (165 kDa).

b) ErbB-2/3 cotransfected cells were immunoprecipitated with anti-ErbB-2 antibody, and phosphotyrosine, ErbB-3 and ErbB-2 were detected by Western blot (from top to bottom panels, respectively). Note that NRG-1 enhanced the tyrosine phosphorylation level and the interaction of ErbB-2 and ErbB-3. Thus. ErbB-2/ErbB-3 interactions are shown by this coimmunoprecipitation experiment.

Figure 2:
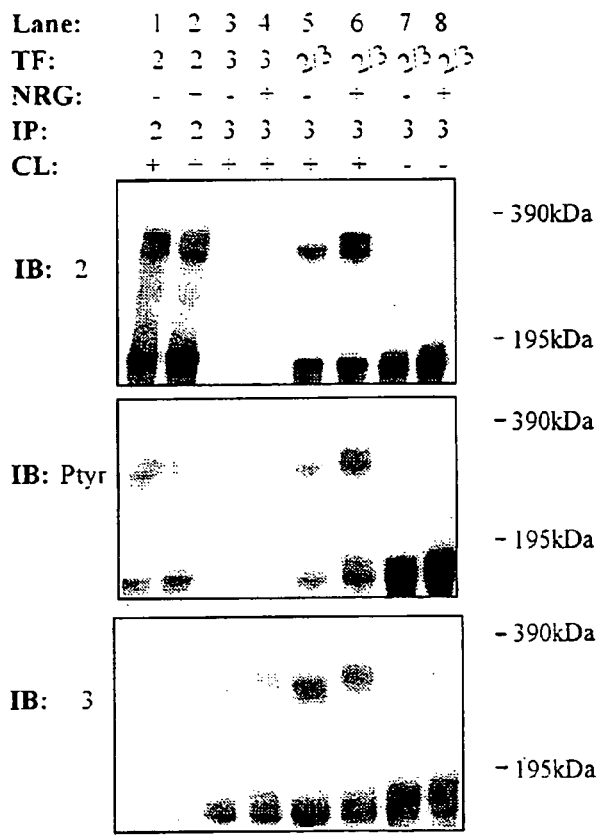
Figure 2:
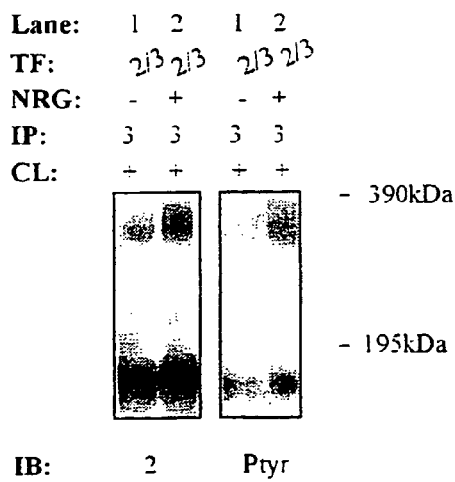

FIG. 2. ErbB-2 and ErbB-3 form heterodimers ErbB-2 and ErbB-3 cotransfected NIH3T3 cells and the heterodimers identified by cross-linking experiments.

a) ErbB-2. ErbB-3, or ErbB-2/3 cotransfected cells were serum starved for 12 h. The control cells were stimulated with HRG b1 for 10 min. The cross-linking was carried out with BS3 reagent for 30 min at room temperature. The cells were lysed and immunoprecipitated with anti-ErbB-2 or anti-ErbB-3 antibodies, and the precipitants subjected to 4% PAGE and Western blot analysis with anti-ErbB-2 antibody (top panel), anti-phospho-tyrosine antibody (middle panel), and anti-ErbB-3 antibody (bottom panel). The position of the dimers and monomers are shown. Note that NGR-1 caused a banding shift for the heterodimer but did not affect the banding pattern of the homodimer.

b) A similar cross-linking assay of non serum-starved ErbB-2 and ErbB-3 cotransfected cells. As above, the dimers and monomers are indicated; note that a similar banding shift in the dimer is seen in response to NRG-1 stimulation.

Figure 3:
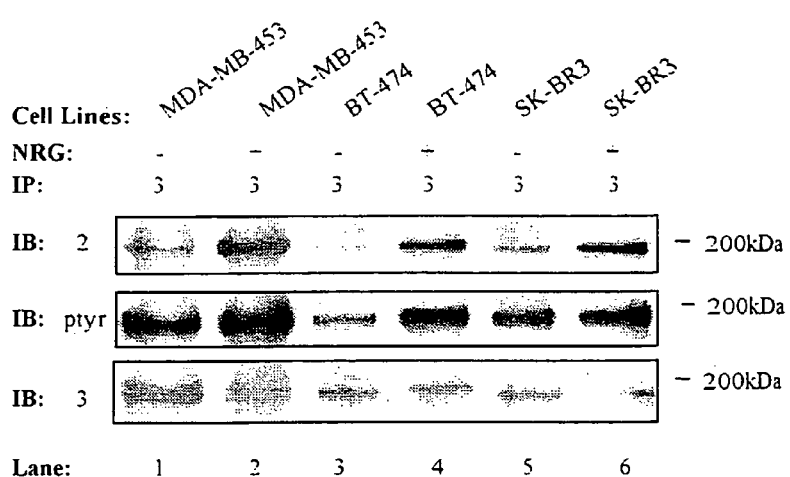

FIG. 3. The ErbB-2 and ErbB-3 heterodimers are identified in human breast cancer cells in the absence of the ligand, neuregulin-1. MDA-MB-453, BT-474 and SK-BR-3 cells were starved in serum free medium for 24 h, and then stimulated with NRG-1. The cells were lysed and immunoprecipitated with anti-ErbB-3 antibody. The precipitants were then separated on 8% SDS-PAGE and subjected to Western blot analysis with anti-ErbB-2 antibody (top panel), anti-phosphotyrosine antibody (middle panel) and anti-ErbB-3 antibody (bottom panel). In all cell lines, ErbB-2 receptors coimmunoprecipitated with the anti-ErbB-3 antibody. The NRG-1 significantly enhanced the interaction of ErbB-2 and ErbB-3 receptors in these breast cancer cell lines (top panel). NRG-1 was also shown to elevate the level of tyrosine phosphorylation (middle panel).

Figure 4:
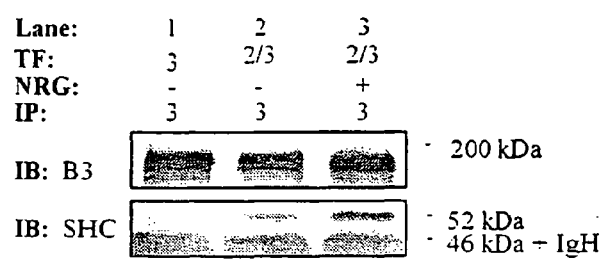
Figure 4:
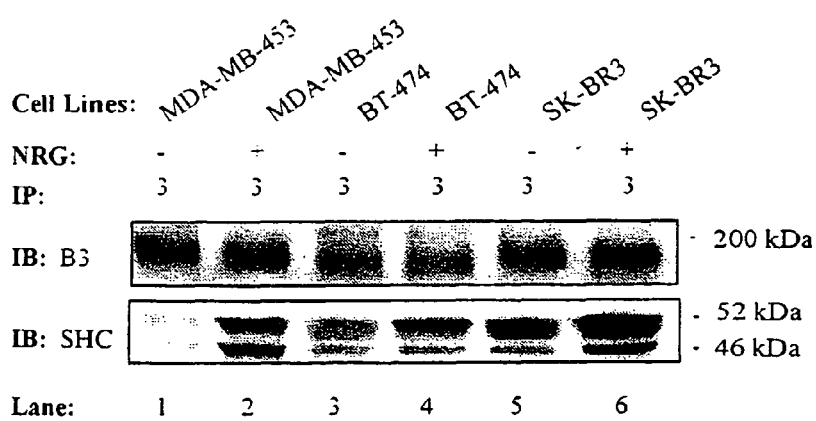

FIG. 4. ErbB-3 binds to signalling protein. Shc, in ErbB-2 and ErbB-3 cotransfected NIH3T3 and human breast cancer cells in the absence of the ligand.

a) ErbB-2. ErbB-3 or ErbB-2/3 cotransfected NIH3T3 cells were serum starved for 12 h and treated with NRG-1. The cell lysates were immunoprecipitated with anti-ErbB-3 antibodies and analysed by SDS-PAGE followed by Western blot. Coimmunoprecipitation of Shc with anti-ErbB-2 and -ErbB-3 antibodies was detected by a specific anti-Shc antibody. FIG. 4a shows that the 46 kD and 52 kD Shc isoforms were coprecipitated by anti-ErbB-2 antibody in ErbB-2 alone and ErbB-2/3 cotransfected cells, and NRG-1 appears to enhance Shc binding to the receptors (bottom panel). The upper panel shows ErbB-2 receptors detected by anti-ErbB-2 antibody in these transfected cells.

b) The two Shc isoforms were coimmunoprecipitated by anti-ErbB-3 antibody in breast cancer cells. Note that the Shc could not bind ErbB-3 receptors in ErbB-3 alone transfected cell. The four human breast cancer cell lines were starved in serum-free medium for 12 hour and then stimulated with the ligand, HRG b1 for 10 min. as marked. Cells were then harvested and subjected to immunoprecipitation with anti-ErbB-3 antibody.

c) Precipitated ErbB-3 was detected by the anti-ErbB-3 antibody for normalisation of amount of ErbB-3 protein.

Figure 5:
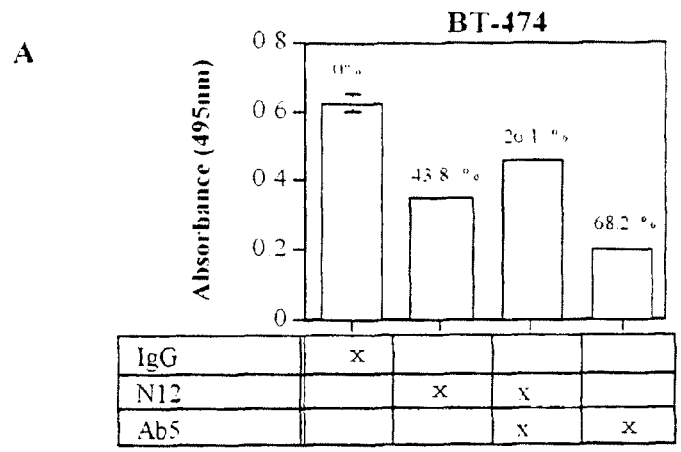
Figure 5:
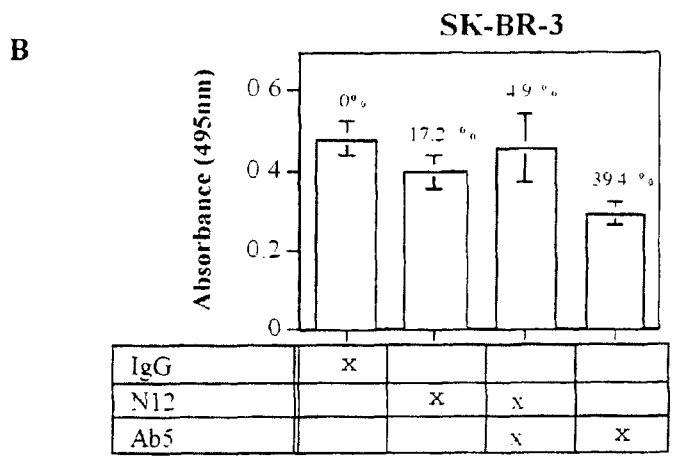
Figure 5:
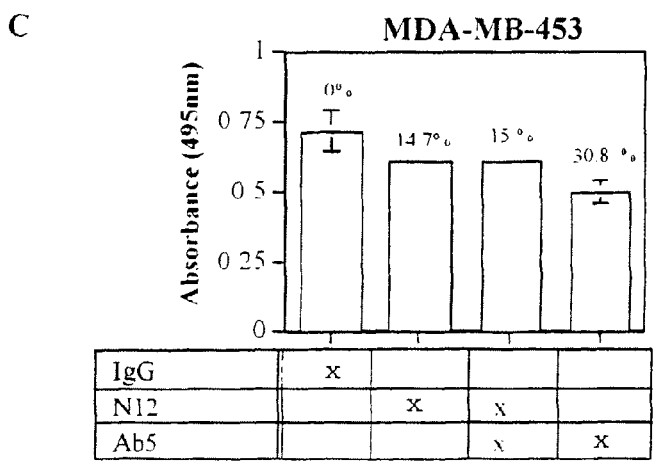

FIG. 5. Anti-ErbB-2 and anti-ErbB-3 antibody-mediated growth inhibition of human breast cancer cells in the absence of the ligand, neuregulin-1, (A) BT-474, (B) SK-BR-3 and (C) MDA-MB-453 human breast cancer cell lines were seeded in 96 well plates at a concentration of 2000 cells per well. After adhering to the plates (16 hr) cultures were treated with antibodies as indicated. The concentration of each antibody was as follows:—IgG 5 mg/ml; Ab5 (anti-ErbB-3 antibody); 2.5 mg/ml; N12 (anti-ErbB-2 antibody) 2.5 mg/ml. Cultures were left to grow for 14 days, media and antibodies were replenished at day 7. After 14 days cell numbers were established using the CellTiter 96® AQueous non-radioactive cell proliferation kit (Promega).

Figure 6A:
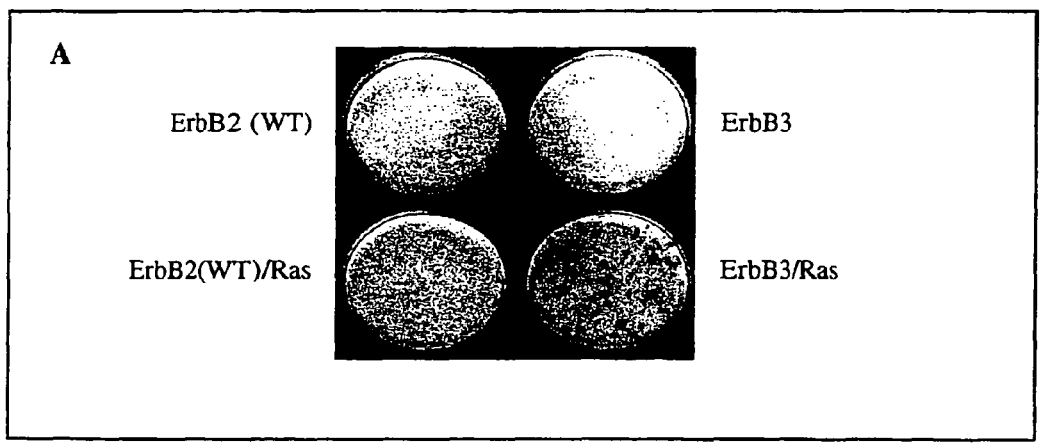
Figure 6B:
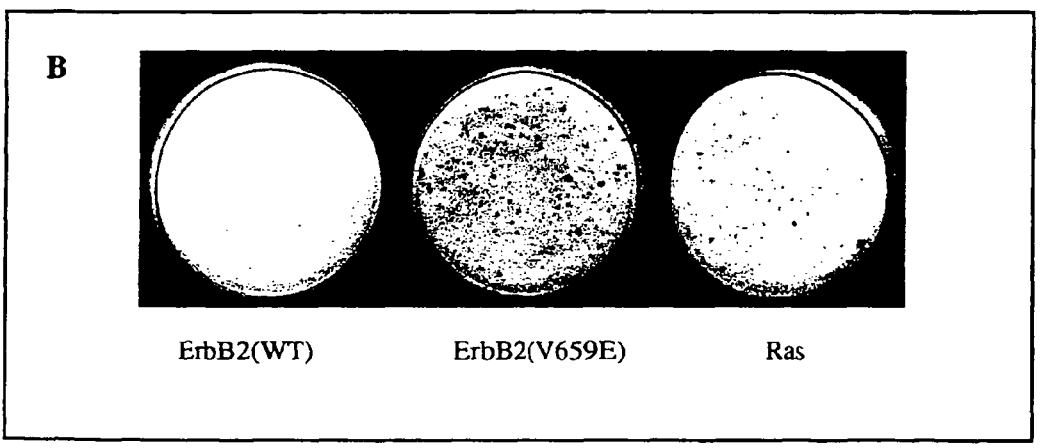

FIG. 6. Focus formation of ErbB constructs transfected NIH3T3 cells. Cells transfected with wild-type ErbB-2 or ErbB-3 (WT) (upper row), or co-transfected with ErbB-2/ H-ras. ErbB-3/H-ras as indicated in panel A, were cultured for focus formation. Wild-type ErbB-2 (WT). ErbB-2 V/E659659 mutant (V659E), or H-ras alone was transfected in cells for focus formation as shown in panel B. Foci were revealed by Xylene staining.

MODES FOR CARRYING OUT THE INVENTION

Experimental Procedures

Materials

NIH3T3 cell line and breast cancer cell lines. SK-BR-3. MDA-MB-453 and BT-474 were purchased from American Type Culture Collection. LipofectAMINE™ transfection reagent was obtained from Life Technologies, Inc. NRG-1, and the antibodies N12 and H3.105.5 were purchased from Neo Markers. The cross-linking reagent BS3 was obtained from PIERCE Chemical Company. The ErbB-2 expression plasmid pRC/CMV-ErbB-2 encoding a full length human ErbB-2 cDNA and ErbB-3 expression plasmid pCMVneo-HER3 encoding a full length human ErbB-3 cDNA were kindly provided by Drs Rodney Fiddes and Roger Daly (The Garvan Institute of Medical Research, Darlinghurst, NSW 2010, Australia). Antibodies recognising ErbB-2 (NCL-CB11 and NCL-PC11) were purchased from Novocastra Laboratories Ltd. Anti-ErbB-3 was purchased from Santa Cruz Biotechnology. Anti-Shc, anti-phosphotyrosine (Recombinant RC20:HRPO) was purchased from Transduction Laboratories. Horseradish peroxidase-conjugated secondary antibodies and enhanced chemiluminescence (ECL) regents were purchased from NEN Life Science Products.

Cell Culture and Transient Transfections

NIH3T3 or human breast cancer cells were maintained in Dulbecco's modified Eagle medium (DMEM) supplemented with 10% foetal bovine serum (FBS) and the selective antibiotic at 37° C. in a 5% $CO_2$ atmosphere. NIH3T3 were transfected with ErbB-2 and ErbB-3 DNA plasmid individually or in combination using the LipofectAMINE™ reagent according to the manufacturer's instructions. Experiments were initiated 48 h after transfection. Prior to growth factor stimulation, cells were starved for 18 hours in DMEM.

Immunoprecipitation and Western Blot Analysis

For analysis of ErbB receptors and associated proteins, transfected cells ($1-2\times10^6$) were washed with cold PBS and solubilized in 1 ml of lysis buffer (50 mM Tris[pH 7.4], 5 mM EDTA, 150 mM NaCl, 1% Triton X-100, 2 mM sodium orthovanadate, 50 mM sodium fluoride, 2 mM phenylmethylsulfonyl fluoride, protease inhibitor cocktail on ice (Boeringher). The lysates were incubated with protein A (Sigma) or protein G (Amersham Pharmacia Biotech) Sepharose at 4° C. for 60 min on a orbital rotor before being clarified by centrifugation at 13000 g for 15 min. For immunoprecipitations, cell Mates were incubated with specific antibodies for 60 min at 4° C. Immuno complexes were collected with protein A or protein G Sepharose and washed four times with lysis buffer. Cell lysates or immunoprecipitated proteins were solubilized by boiling in sample buffer and were subjected to SDS-PAGE. The proteins were electrotransferred to PVDF membranes. After blocking with 5% skim milk in PBS with 0.02% Tween 20 at 4° C. overnight, membranes were probed with primary antibodies followed by secondary antibodies, each for 60 min at room temperature. Proteins were visualised with peroxidase-coupled secondary antibody by using an enhanced chemiluminescence reagent (NEN Life Science Products). For reprobing, the blotted membranes were stripped with 1% SDS, 0.2 M Tris pH 8.0 by shaking at RT for 2 hours, then were probed with respective antibodies.

Chemical Cross Link Assay

Before cross-linking and immunoprecipitation assays, the transfected cells were starved overnight in serum-free media (DMEM). The following day the cells were treated with 50 nM NRG-1 (Neo Markers) in serum-free medium for 10 min. Cultures were washed three times in PBS before being treated with the cell impermeable cross-linking reagent $BS^3$ (PIERCE) (2 mM in PBS) at room temperature for 30 min. Then the cross-linking reaction was stopped with 10 min Tris pH 7.5, 0.9% NaCl and 0.1 M glycine for 15 min at room temperature. The whole cell lysates were prepared with lysis buffer and immediately subjected to immunoprecipitation assay as described above.

Antibody-Mediated Cell Growth Inhibition

SK-BR-3. MDA-MB-453, BT474, MCF-7 and T47D cells were treated with antibodies specific for ErbB-2 and/or ErbB-3. The anti-ErbB-2 antibody used was N12 which is known to inhibit the growth of various cancer cell lines that over-express ErbB-2. The anti-ErbB-3 antibody used was H3.105.5, which is reported not to affect the growth of cancer cell lines over-expressing ErbB-3 (Neomarkers catalogue). Both antibodies are of the same isotype (IgG1) and recognise the extracellular region of the receptor. Cells were seeded in 96 well plates at a density of 5000 cells/well and left to adhere for 16 hours. Antibodies were then added to wells (N12—1 mg/ml; H3.105.5 2.5 mg/ml, crude mouse IgG—5 mg/ml) and cultures were incubated for a further 5 days. The number of cells in each well was determined using the Cell Titre AQueous proliferation assay (Promega), following the manufacturers protocol.

Introduction

ErbBs are class one receptor protein tyrosine kinases. ErbB-mediated cell signalling plays a critical role in embryo development and adult organ function. On a cellular level the ErbB receptors have been shown to mediate signals for cell proliferation, differentiation, migration, and cell structure reorganisation. There are four structurally similar ErbB members, ErbB-1, 2, 3 and 4. Epidermal growth factor (EGF) is one of several ligands that bind ErbB-1. ErbB-3 or ErbB-4 also bind several ligands, including neuregulin-1 (NRG-1). To date, no ligand for ErbB-2 has been identified. However, ErbB-2 serves as an heterodimer partner for ErbB-3, ErbB-4 or ErbB-1, and is critically involved in NRG-1-activated cell signalling.

In vivo studies using gene targeting experiments indicate that developmental defects resulting from inactivation of ErbB-2 are similar to those observed in NRG-1-inactivated animals. Both animals showed defects in the neural crania ganglia and heart trabeculae development. Furthermore, ErbB-3 or ErbB-4 gene-inactivated mice have similar or overlapping phenotypes to NRG-1 or ErbB-2 knockout mice. This strongly suggests that ErbB-2 participates in NRG-1-activated ErbB-3 or ErbB-4 signalling pathways in vivo.

In addition to its role in development, the human ErbB-2 gene is frequently amplified and its encoded protein is over-expressed in a variety of human carcinomas. Early research on ErbB-2 discovered that an oncogenic point mutation resulted in the formation of ErbB-2 homodimers that in turn caused significant phosphorylation of the tyrosine residues on the intracellular domain. While no corresponding point mutation has been found in ErbB-2 overexpressing human carcinomas, the upregulation of ErbB-2 results in the formation of homodimers that in turn increases the tyrosine phosphorylation of its intracellular domain. This process is hypothesised to be the start of a signal cascade that triggers cell transformation and/or growth, and thus initiate tumourigenesis. However, there is evidence to contradict the hypothesis that ErbB-2 homodimers are responsible for the initiation of tumourigenesis: i) some ErbB-2 mutants that are engineered to enhanced dimerisation and self-phosphorylation have no effect on cell transformation: ii) antibodies that bind to the extracellular domain of ErbB-2 and presumably promote homodimerisation result in ErbB-2-expressing cancer cell growth promotion, whereas others inhibit cancer cell growth. These data indicate that homodimerisation of ErbB-2 is insufficient for cell growth promotion or cell transformation, and other conditions, possibly involving specific dimer orientation or conformation, are required.

ErbB-2 acts as a heterodimer partner for the ligand-binding ErbB-3 or ErbB-4 receptors. The ligand, NRG-1, has been identified to have two independent receptor binding sites: one that has a high affinity for ErbB-3 or ErbB-4, and the other that has a low but non-specific affinity for all ErbB members. Thus the exposure of NRG-1 to cells expressing ErbB-3/4 and ErbB-2 would result in heterodimers of ErbB-2 and ErbB-3/4. However, in the absence of the ligand it is unclear whether ErbB-2 has an affinity with other ErbB receptors, and it is possible that such an interaction could be involved in the initiation of cancer. Amongst all the ErbB receptors ErbB-3 is unique because: i) ErbB-2 preferentially forms heterodimers with ErbB-3; ii) co-transfection of NIH3T3 cells with ErbB-2 and ErbB-3 results in much higher levels of cell transformation than that of transfection with ErbB-2 alone; iii) in ErbB-2 over-expression-associated breast cancer cells, ErbB-3 is also highly expressed; iv) ErbB-3 is also overexpressed in ErbB-2-overexpressing tumour cells from ErbB-2 transgenic mice.

The present inventors examined whether ErbB-2 and ErbB-3 interacted in a ligand independent manner in NIH3T3 cells cotransfected with the two receptors. By co-immunoprecipitation, ErbB-2 was detected in ErbB-3 precipitants from cells cultured in the absence of NRG-1, and conversely ErbB-3 was detected in ErbB-2 precipitants. ErbB-2/3 complexes were also identified in cross linking experiments. The ligand-dependent and ligand-independent ErbB-2/ErbB-3 heterodimers were distinguished by the distinct mobilities of the two cross-linked dimers on the SDS-PAGE. However, both ErbB-2 and ErbB-3 in the ligand-independent heterodimer are phosphorylated and bind to Shc, an intracellular cell signalling protein. These ligand-independent ErbB-2/ErbB-3 heterodimers were also detected in cells from ErbB-2-overexpressing human breast cancer lines. SK-BR-3, TB-474, and MDA-MB-453. To test whether the ligand-independent heterodimer is able to activate cell growth in breast cancers, the above three human breast cancer cell lines were treated with anti-ErbB-2 extracellular domain and anti-ErbB-3 extracellular domain antibodies in a cell growth assay. The anti-ErbB-2 antibody. N12, suppressed growth in all three cancer cell lines, while the anti-ErbB-3 antibody reduced the growth in BT-474 and MDA-MB-453 cancer cell lines. Interestingly, when ErbB-2 antibody was combined with ErbB-3 antibody in cultures of SK-BR-3 cancer cells, the two antibodies had a synergistic inhibitory effect on cancer cell growth. These results indicate that ErbB-3 is involved in human breast cancer cell growth by ligand-independent heterodimerisation with ErbB-2.

Results

Figure 1:
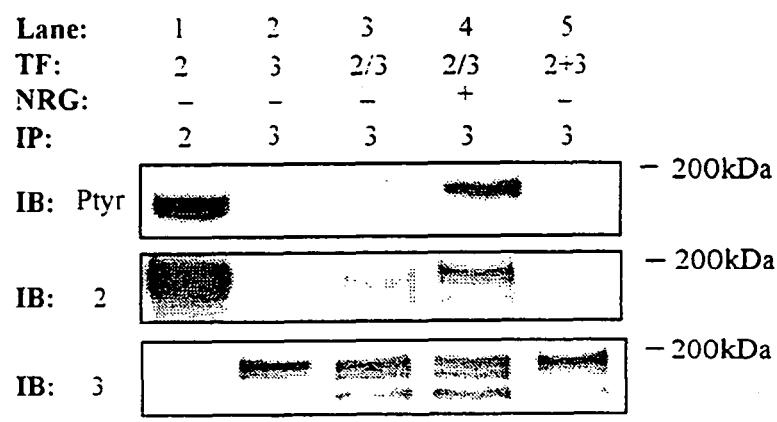
FIG. 1. ErbB-2 interacts with ErbB-3 in ErbB-2/ErbB-3 co-transfected NIH3T3 cells in the absence of NRG-1. NIH3T3 cells were transiently transfected with ErbB-2, ErbB-3, or ErbB-2 with ErbB-3. After 48 hours, one cotransfected sample was treated with Neuregulin 1 (NRG-1) (50 nM) for 10 min. The cells were lysed and the receptors immunoprecipitated with anti-ErbB-2 or anti-ErbB-3 antibodies. The precipitants were separated by 8% PAGE and analysed by Western blot.
Figure 1:
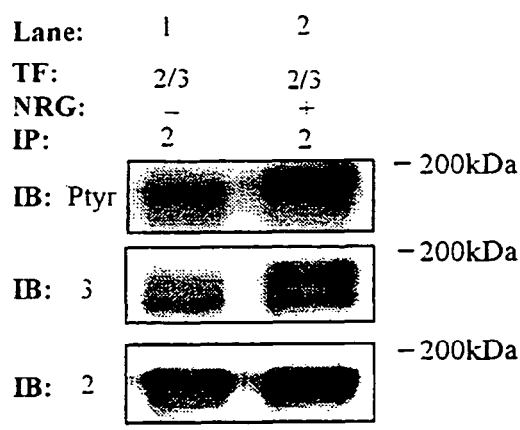

To investigate ErbB-2 and ErbB-3 interactions in the absence of NRG-1, the present inventors used NIH3T3 cells, which express low levels of ErbB-2 and no detectable levels of the other ErbB receptors, and transiently expressed either ErbB-2. ErbB-3 or both ErbB-2 and ErbB-3. To avoid possible NRG-1 in the serum of the cell culture medium, cells were cultured in serum-free medium for 24 h prior to harvesting. ErbB-2 or ErbB-3 were then precipitated using antibodies specific for either receptor, and precipitants were analysed by Western blot. Immunoblots using anti-ErbB-2 antibodies detected ErbB-2 in ErbB-3 precipitants (FIG. 1a, middle panel, Lane 3). This was not a cross reaction of the antibodies as the anti-ErbB-3 antibody was not able to precipitate ErbB-2 (FIG. 1a, middle panel, Lane 5) or bind to ErbB-2 in the Western blot (FIG. 1a bottom panel. Lane 1). Similarly, the anti-ErbB-2 antibody was not able to precipitate ErbB-3 (FIG. 1a, bottom panel. Lane 1) or bind to ErbB-3 on the Western blot (FIG. 1a, middle panel Lane 2). The complex formation required membrane association of ErbB-2 and ErbB-3, as soluble receptors are not capable of forming the complex in mixed cell extracts of cells transfected with ErbB-2 and ErbB-3 separately (FIG. 1a, middle panel, Lane 5). ErbB-3 receptors were also detected by Western immunoblotting of anti-ErbB-2 precipitates from ErbB-2/3 contransfected NIH3T3 cells (FIG. 1b). The presence of NRG-1 enhanced the heterodimerisation of ErbB-2 and ErbB-3 as expected (FIG. 1a. Lane 4; FIG. 1b. Lane 2).

Immunoblotting detected the presence of phosphorylated tyrosines of an 180 kDa protein from ErbB-2/3 cells treated with or without NRG-1 (FIG. 1a, top panel. Lane 3 and 4, respectively). It is expected that this phosphorylation was present on intracellular ErbB-2 and/or ErbB-3 that had formed a ligand independent heterodimer. Unlike ErbB-2, ErbB-3 has an impaired kinase domain and would not be capable of phosphorylating other proteins. Therefore, this indicates that the phosphorylated protein is most likely ErbB-3.

To test whether the ErbB-2 and ErbB-3 complex detected by coimmunoprecipitation is a heterodimer, cross-linking experiments were performed with cells transfected with ErbB-2 or ErbB-3 alone, or cotransfected with ErbB-2 and ErbB-3. The cell lysates were immunoprecipitated with anti-ErbB-2 or anti-ErbB-3 antibodies. ErbB-2 overexpression results in homodimerisation, as doublet protein bands were detected at approximately 360 kDa while the monomeric receptor was detected at approximately 180 kDa (FIG. 2a, top panel. Lane 1). Formation of the ErbB-2 homodimer was independent of ligand stimulation (FIG. 2a, top panel, Lanes 1 vs 2).

A 360 kDa dimer was also detected in ErbB-2/ErbB-3 co-transfected cells (FIG. 2a. Lane 5). This was a heterodimer, as the protein was precipitated with anti-ErbB-3 antibody and detected on the Western blot with anti-ErbB-2 antibody. However, unlike the ErbB-2 homodimer, the ErbB-2/ErbB-3 heterodimer consisted of only a single band. In response to NRG-1 stimulation of ErbB-2/ErbB-3 cotransfected cells, there was a lower mobility heterodimer complex similar to that seen in ErbB-2 transfected cells (FIG. 2a, top panel. Lane 1 vs 6). The decrease in mobility of the ligand-activated heterodimer was not due to increased tyrosine phosphorylation, since i) the doublet dimers are both phosphorylated on tyrosine residues; and ii) both ligand-dependent and ligand-independent heterodimers had similar levels of tyrosine phosphorylation (FIG. 2a, middle panel. Lanes 5 and 6). Once again the presence of ErbB-2/3 heterodimers was not the result of cross reactivity of the antibodies as the ErbB-2 homodimers were not detected by the anti-ErbB-3 antibody (FIG. 2a, bottom panel. Lanes 1 and 2). ErbB-3 was only capable of forming a limited amount of homodimers, even in the presence of NRG-1 (FIG. 2a, bottom panel, Lanes 3 and 4).

In order to test whether the heterodimerisation of ErbB-2 and ErbB-3 could be stimulated by a unknown ligand in serum. ErbB-2/ErbB-3 cotransfected cells were cultured in either serum free media or in media containing serum. As shown in FIG. 2b, left and right panels, similar banding patterns are detected from cells cultured with or without serum.

To test whether the ErbB-2 and ErbB-3 overexpression-mediated heterodimer formation in NIH3T3 cells had any relevance to cancer cells which overexpress ErbB-2, the human breast cancer cell lines SK-BR-3, MDA-MB-453, and BT-474, which overexpress ErbB-2 and ErbB-3 were studied. As in the cotransfected NIH3T3 cells. ErbB-2 co-precipitated with ErbB-3 using the anti-ErbB-3 antibody (FIG. 3a). Also, consistent with data from cotransfected NIH3T3 cells, NRG-1 significantly enhanced the formation of ErbB-2/3 heterodimers in these cells (FIG. 3a).

Since ligand-stimulated ErbB-2/ErbB-3 heterodimers are known to bind to the cell signalling molecule Shc, the present inventors examined whether the ligand-independent ErbB-2/ErbB-3 heterodimers also bind to Shc. Similar amounts of Shc co-immunoprecipitated with ErbB-2 from ErbB-2 transfected cells and ErbB-2/3 co-transfected cells, in the absence of NRG-1 (FIG. 4a, Lanes 1 and 2). As the overexpression of ErbB-2 in NIH3T3 cells resulted in ErbB-2 homodimers (FIG. 2a), this data shows that Shc can bind to ErbB-2 homodimers. However. Shc also co-immunoprecipitated with ErbB-3 from ErbB-2/3 transfected cells in the absence and presence of NRG-1 (FIG. 4b, Lanes 2 and 3). As Shc did not co-immunoprecipitate with ErbB-3 from cells expressing ErbB-3 alone, this data indicates that Shc is associated with ErbB-2/3 heterodimers in the presence and absence of NRG-1.

Next it was examined whether Shc also associated with ErbB-2/3 heterodimers in human breast cancer cells. Once again, Shc was found to co-immunoprecipitate with ErbB-3 from each cancer cell line (FIG. 4c). In each cell line tested, NRG-1 enhanced the co-immunoprecipitation of Shc with ErbB-3, indicating that Shc does interact with ErbB-2/3 heterodimers.

To test if the ligand-independent ErbB-2/ErbB-3 heterodimers are active in cell signalling and in stimulation of cell growth, commercial anti-ErbB-2 (N12) and anti-ErbB-3 (Ab5) extracellular domain antibodies were used to treat cultures of human breast cancer cells that over-express ErbB-2 and ErbB-3. It was predicted that the combination of these antibodies would disrupt preformed ErbB-2/3 heterodimers and thus disrupt their signalling properties and possibly the stimulation of cell growth. N12 has previously been reported to inhibit the growth of various cancer cell lines, and here it is confirmed that the antibody inhibits anchorage dependent growth of cancer cell lines, including MDA-MB-453. BT-474, and SK-BR-3 cells (FIG. 5). BT-474 cells were more sensitive to N12 compared to the other cell lines. However, it was found that Ab5 also inhibited growth in both BT-474 and MDA-MB-453 cells (FIGS. 5a and b, respectively). As with N12, BT-474 cells were more sensitive to Ab5 in comparison to other cancer cell lines tested. When N12 and Ab5 were combined to treat these breast cancer cells, they had an additive effect on MDA-MB-453 and BT-474 cells, and a synergistic effect on SK-BR-3 cells. T47D and MCF-7 cells were also tested with this cell growth assay. In T47D cells. ErbB-2 and ErbB-3 are overexpressed, and in MCF-7 cells ErbB-1, 3 and 4 are highly expressed. However, neither of the cells responds to N12 or Ab5, indicating that the growth activity of ErbB-3 is dependent on the presence of active ErbB-2 (which is able to respond to anti-ErbB-2 antibody (data not shown). Thus, it was concluded that ErbB-2/3 heterodimers are active in many human breast cancer cells even in the absence of a ligand, and this heterodimer is responsible for stimulating cell growth.

Discussion

Overall, the present inventors have shown a cell growth stimulation effect triggered by ErbB-2/ErbB-3 in the absence of the ligand. NRG-1. This is associated with over-expression of ErbB-2 and ErbB-3 in human breast cancer cells. This finding is supported by the following observations: i) over-expressed ErbB-2 and ErbB-3 form heterodimers in ErbB-2/ErbB-3 co-transfected NIH3T3 cells, and in ErbB-2 over-expressing human breast cancer cells, which respond to anti-ErbB-2 antibody's inhibitory effect; ii) in the ligand independent ErbB-2/ErbB-3 heterodimers. ErbB-3 is phosphorylated on tyrosine residues; iii) the ligand-independent heterodimer binds to the cell signalling molecule Shc; iv) a commercial anti-ErbB-3 antibody, which has previously been reported not to have inhibitory effect on cancer cells, inhibits human breast cancer cell growth, and when it is combined with an anti-ErbB-2 antibody, they show either additive or synergistic effect on cell growth inhibition. Thus, it is concluded that ErbB-3 is involved in human breast cancer cell growth via a ligand-independent interaction with over-expressed ErbB-2.

Early studies postulated that ErbB-2 over-expression alone was enough to induce tumourigenesis. Such conclusions were made from the following observations: i) ErbB-2 is over-expressed in a variety of human cancer cells since the ErbB-2 gene is amplified: ii) ErbB-2 over-expression results in phosphorylation of its intracellular domain and binding to cell signalling proteins. Shc and Grb2: iii) transfection of cultured fibroblast cells with the wild-type ErbB-2 gene results in cell transformation; and iv) ErbB-2 mutant, in which homodimerisation is enhanced, shows a higher level of the transformation activity. However, although ErbB-2 mutant is able to transform cells, it is not clear if the wild-type ErbB-2 can also transform cells, since other studies can not identify such an activity for ErbB-2 alone. It is not clear if in these a few ErbB-2 transformed cells. ErbB-3 is also expressed, as such an ErbB-3 expression occurred in tumour cells from the ErbB-2 transgenic line. Thus, even though ErbB-2 is involved in cancer cell growth or cell transformation, it not clear if ErbB-2 alone is sufficient in mediating cell signals for cell growth or transformation. It is possible that only the ErbB-2/ErbB-3 heterodimer but not the ErbB-2 homodimer is directly involved in tumourigenesis.

This study indicates that without ligand binding, ErbB-2 and ErbB-3 heterodimeric complexes exist on the cell surface in ErbB-2-overexpressing and ErbB-3 highly-expressing cells. This is supported by the co-immunoprecipitation of ErbB-2 and ErbB-3 from co-transfected NIH3T3 cells. The co-immunoprecipitation is also obtained with cells of the human breast cancer cell lines. SK-BR3. MDA-MB-453 and BT-474, which over-expresses ErbB-2 and express high levels of ErbB-3, but not NRG-1. It is thought that the ligand-independent heterodimer may have a higher affinity to NRG-1 than to the ErbB-3 homodimer. Artificial heterodimers of ErbB-2 and ErbB-3 have a much higher ligand binding affinity than artificial ErbB-3 homodimers or monomers. However, previous studies suggested that the ligand initiated ErbB-2 and ErbB-3 dimerisation. This apparent contradiction has not been adequately explained. Therefore it is unclear from those studies whether the dimer is formed prior to or after ligand binding to ErbB-3. Moreover, the present finding suggests that ligand-independent formation of the ErbB-2-ErbB-3 heterodimeric complex might be dominant over the formation of ErbB-2 homodimers, as the presence of ErbB-3 can prevent formation of ErbB-2 homodimer doublet bands on the SDS-PAGE.

It is unexpected that ligand-dependent ErbB-2/ErbB-3 heterodimers have a lower mobility on SDS-PAGE than that of the ligand-independent heterodimers. This difference may be due to the molecular mass of the ligand. NRG-1, which could be cross-linked to the receptors. However, the ligand used in this experiment contains only an EGF domain of about 7 kDa, thus it is unlikely that the molecular mass of the ligand is able to significantly change the heterodimer mobility. This mobility difference could be due instead to different conformations between the two heterodimers, which are fixed by the cross-linking reagents, or to different levels of phosphorylation, although both heterodimers are phosphorylated at comparable levels detected by the anti-phosphotyrosine antibody.

Another critical aspect of this study is the anti-ErbB-3 antibody-mediated cancer cell growth inhibition. The anti-ErbB-3 antibody used in this study (H3.105.5) has been previously investigated, and was found to have no effect on the growth of cancer cells which express ErbB-3 (NeoMarks Catalogue. 1999). The differing observations could be due to the different cell lines used. Unlike the previous study, the present inventors have tested five human breast cancer cell lines: MCF-7. T47D, SK-BR-3. MDA-MB-453 and BT-474. Cells from the latter two lines respond to the ErbB-3 antibody alone. Interestingly. SK-BR-3 cells do not significantly respond to the ErbB-3 antibody alone but show a 2.5-fold greater response to a combination of ErbB-2 and ErbB-3 antibodies than to the ErbB-2 antibody alone. Critically, all three cell lines which respond the ErbB-3 antibody also respond to the ErbB-2 antibody. MCF-7 and T47D cell respond neither to the ErbB-2 antibody nor the ErbB-3 antibody, even though MCF-7 cells express ErbB-1, 3 and 4, and T47D over-express ErbB-2 and ErbB-3. Given that the anti-ErbB-2 antibody, herceptin, which has been used in breast cancer patients for cancer cell growth suppression, is only effective on 50% patients, the coincidence of the three cells responding to both antibodies, suggests that ErbB-2/ErbB-3 heterodimer may be the only active form in stimulation of cancer cell growth.

One aspect of the present invention is a novel approach for cancer therapy by blocking or interfering with the ErbB-2/ErbB-3 heterodimer formation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of arresting or inhibiting cell growth in the absence of ErbB-3 ligand, which method comprises contacting an ErbB-2 over-expressing cell with a composition comprising a combination of an anti-ErbB-2 extracellular domain antibody and an anti-ErbB-3 antibody, wherein the anti-ErbB-2 extracellular domain antibody is N12 or a humanized N12, and the anti-ErbB-3 antibody is H3.105.5 or a humanized H3.105.5, thereby arresting or inhibiting growth of said ErbB-2 over-expressing cell in the absence of ErbB-3 ligand.

2. The method of claim 1, wherein the anti-ErbB-2 extracellular domain antibody is a monoclonal humanized N12.

3. The method of claim 1, wherein the anti-ErbB-3 antibody is a monoclonal humanized H3.105.5.

4. The method of claim 1, wherein the anti-ErbB-2 extracellular domain antibody is N12.

5. The method of claim 1, wherein the anti-ErbB-3 antibody is H3.105.5.

6. The method of claim 1, wherein the cell is a cancer cell.

7. The method of claim 2, wherein the cell is a cancer cell.

8. The method of claim 3, wherein the cell is a cancer cell.

9. The method of claim 6, wherein the cancer cell is a human breast cancer cell.

10. The method of claim 7, wherein the cancer cell is a human breast cancer cell.

11. The method of claim 8, wherein the cancer cell is a human breast cancer cell.

12. The method of claim 9, wherein the human breast cancer cell is SK-BR-3, MDA-MB-453, or BT-474.

13. A method for treating ErbB-2 over-expressing cancer in the absence of ErbB-3 ligand, comprising administering to a subject in need thereof a composition comprising a combination of an anti-ErbB-2 extracellular domain antibody and an anti-ErbB-3 antibody, wherein the anti-ErbB-2 extracellular domain antibody is N12 or a humanized N12, and the anti-ErbB-3 antibody is H3.105.5 or a humanized H3.105.5, thereby treating ErbB-2 over-expressing cancer in said subject in the absence of ErbB-3 ligand.

14. The method of claim 13, wherein the anti-ErbB-2 extracellular domain antibody is a monoclonal humanized N12.

15. The method of claim 13, wherein the anti-ErbB-3 antibody is a monoclonal humanized H3.105.5.

16. The method of claim 13, wherein the anti-ErbB-2 extracellular domain antibody is N12.

17. The method of claim 13, wherein the anti-ErbB-3 antibody is H3.105.5.

18. The method of claim 13, wherein the cancer is a human breast cancer.

19. The method of claim 14, wherein the cancer is a human breast cancer.

20. The method of claim 15, wherein the cancer is a human breast cancer.

* * * * *